US00PP21955P2

(12) United States Plant Patent
Roberson

(10) Patent No.: US PP21,955 P2
(45) Date of Patent: May 31, 2011

(54) ***CANNA* PLANT NAMED 'CAN DO APRICOT DARK LEAF'**

(50) Latin Name: *Canna generalis*
Varietal Denomination: Can Do Apricot Dark Leaf

(76) Inventor: Robert Roberson, Grain Valley, MO (US)

( * ) Notice: Subject to any disclaimer, the term of this patent is extended or adjusted under 35 U.S.C. 154(b) by 0 days.

(21) Appl. No.: 12/657,102

(22) Filed: Jan. 13, 2010

(51) Int. Cl.
*A01H 5/00* (2006.01)

(52) U.S. Cl. ..... Plt./415

(58) Field of Classification Search ..... Plt./415
See application file for complete search history.

*Primary Examiner* — Annette H Para

(57) ABSTRACT

A new and distinct *Canna* cultivar named 'Can Do Apricot Dark Leaf' is disclosed, characterized by distinctive apricot colored blossoms, dark foliage, characteristically large petals and rapidly self-cleaning petals. The new cultivar is a *Canna*, typically suited for garden and ornamental container use.

1 Drawing Sheet

Figure 1:
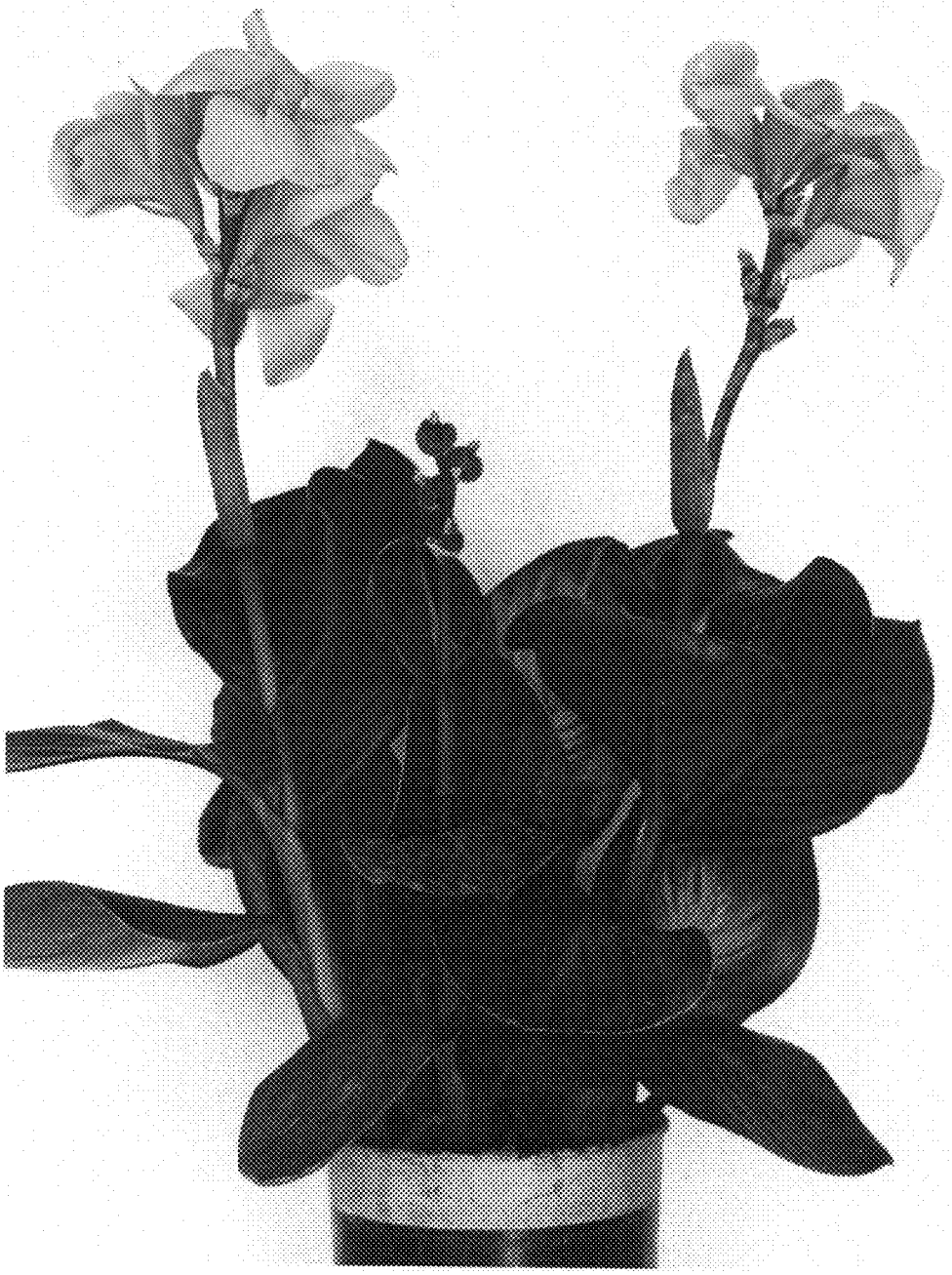

Latin name of the genus and species: *Canna generalis.*
Variety denomination: 'Can Do Apricot Dark Leaf'.

BACKGROUND OF THE INVENTION

The new cultivar is a product of a planned breeding program. The new variety originated from a cross pollination of the seed parent, an unpatented variety of *Canna generalis* known as 'Liberty Coral Rose' with the pollen parent, an unpatented proprietary selection of *Canna generalis* referred to as 'PW-AP-DK04' directed by the inventor in August of 2003. The crossing was made in Grain Valley, Mo., at a commercial greenhouse.

'Can Do Apricot Dark Leaf' was discovered by the inventor, James Roberson, in July 2004 in Grain Valley, Mo., at a commercial greenhouse among seedlings resulting from the 2003 crossing.

Asexual reproduction of the new cultivar 'Can Do Apricot Dark Leaf' was first performed in Grain Valley Mo., at a commercial greenhouse by vegetative divisions in October 2004. 'Can Do Apricot Dark Leaf' has since produced at least five generations and has shown that the unique features of this cultivar are stable and reproduced true to type.

SUMMARY OF THE INVENTION

The cultivar 'Can Do Apricot Dark Leaf' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Can Do Apricot Dark Leaf.' These characteristics in combination distinguish 'Can Do Apricot Dark Leaf' as a new and distinct *Canna* cultivar:

1. Distinctive apricot colored blossoms.
2. Dark foliage coloration.
3. Large petals and overall bloom size.
4. Rapid self cleaning flowering habit.

PARENTAL COMPARISON

Plants of the new cultivar 'Can Do Apricot Dark Leaf' are similar to the female parent 'Liberty Coral Rose' in most horticultural characteristics. However, 'Can Do Apricot Dark Leaf' differs in producing shorter, flowers of a different color. Additionally, 'Can Do Apricot Dark Leaf' produces darker colored foliage, than 'Liberty Coral Rose' and Can produces a more Salmon Pink flower. 'Can Do Apricot Dark Leaf' also produces less seed than 'Liberty Coral Rose.'

Plants of the new cultivar 'Can Do Apricot Dark Leaf' are similar to the male parent 'PW-AP-DK04' in most horticultural characteristics. However, 'Can Do Apricot Dark Leaf' differs in producing a shorter, more compact plant. Additionally, blooms of 'Can Do Apricot Dark Leaf' are a different color and self clean spent petals faster.

COMMERCIAL COMPARISON

'Can Do Apricot Dark Leaf' can be compared to the unpatented commercial variety *Canna* 'Futurity Pink.' Plants of 'Futurity Pink' are similar to plants of 'Can Do Apricot Dark Leaf' in most horticultural characteristics, however, 'Can Do Apricot Dark Leaf' produces a fuller, more compact bloom head than 'Futurity Pink' with wider petals. Additionally, plants of 'Can Do Apricot Dark Leaf' produces flowers of apricot, rather than the salmon pink of 'Futurity Pink.'

'Can Do Apricot Dark Leaf' can also be compared to the unpatented commercial variety *Canna* 'Liberty Watermelon.' Plants of 'Liberty Watermelon' are similar to plants of 'Can Do Apricot Dark Leaf' in most horticultural characteristics, however, 'Can Do Apricot Dark Leaf' produces a shorter, more compact overall plant. Additionally, plants of 'Can Do Apricot Dark Leaf' produces flowers of lighter pink than those of 'Liberty Watermelon.'

BRIEF DESCRIPTION OF THE PHOTOGRAPH

The accompanying photograph in FIG. 1 illustrates in full color a typical plant of 'Can Do Apricot Dark Leaf' grown outdoors in Lompoc, Calif. This plant is approximately 1 year old, shown in a 1 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Can Do Apricot Dark Leaf' plants grown in a greenhouse in Lompoc, Calif. Temperatures ranged from 10° C. to 20° C. at night to 12° C. to 25° C. during the day. No artificial light, photoperiodic treatments or chemical treatments were given to the plants. Measurements and numerical values represent averages of typical plant types.

Botanical classification: *Canna generalis.* cultivar 'Can Do Apricot Dark Leaf.'

Age of the plant described: Approximately 1 year.

Container size of the plant described: 1 gallon.

PROPAGATION

Time to initiate roots: About 5 days at temperatures of 25 to 28 degrees C.

Time to develop roots: About 21 days at temperatures of 28 to 31 degrees C.

Rhizome description: Near RHS White 155A in color covered with papery scale-like leaves near Brown 200B.

Root description: Thick, fibrous near RHS 158C in color.

PLANT

Growth habit: Upright.

Age of plant described: Approximately 1 year.

Container size: 1 gallon nursery container.

Height: Measured from top soil line of pot, approximately 34 cm to top of highest leaf. Approximately 57 cm to top of highest inflorescence.

Plant spread: Approximately 60 cm.

Growth rate: Rapid.

Branching characteristics: Non-branching, basal clump forming.

Stem:

*Length.*—Approximately 34 cm.

*Diameter.*—Approximately 1.9 cm.

*Texture.*—Glabrous.

*Color.*—Background Near RHS Yellow-Green 147A, stripes near RHS Red-Purple 59A.

FOLIAGE

Leaf:

*Arrangement.*—Simple, alternate.

*Average length.*—Approximately 22 cm.

*Average width.*—Approximately 13 cm.

*Shape of blade.*—Ovate.

*Apex.*—Acute.

*Base.*—Symmetrical cuneate with sheathing.

*Margin.*—Entire.

*Texture of top surface.*—Matte, very slightly ridged from veins.

*Texture of bottom surface.*—Smooth, matte.

*Quantity of leaves per plant.*—Approximately 24.

*Color.*—Young foliage upper side: Background Near RHS Yellow-Green 147A with overlay coloration of Red-Purple 59A, striping from veins of Red-Purple 59A. Young foliage under side: Background Near RHS Yellow-Green 147A with overlay coloration of Red-Purple 59A, striping from veins of Red-Purple 59A. Mature foliage upper side: Background Near RHS Yellow-Green 147A striping from veins near Red-Purple 59A. Mature foliage under side: Background Near RHS Yellow-Green 147A, faint striping from veins near Red-Purple 59A.

*Venation.*—Type: Pinnate. Venation color upper side: Near RHS Red-Purple 59A. Venation color under side: Near RHS Red-Purple 59A.

Petiole:

*Length.*—Average 2.5 cm.

*Diameter.*—Average 0.8 cm.

*Texture.*—Glabrous.

*Color.*—Near RHS Yellow-Green 146A with stripes near Red-Purple 59A.

Sheath:

*Length.*—Approximately 5.5 cm.

*Width.*—Approximately 0.8 cm.

*Texture.*—Glabrous.

*Color.*—Near RHS Yellow-Green 146A with stripes near Red-Purple 59A.

FLOWER

Natural flowering season: Spring and Summer.

Inflorescence description: Single flowers arranged on terminal racemes; several racemes per plant.

Flower longevity on plant: Individual flowers last approximately 3 weeks.

Quantity of flowers: Approximately 10 per raceme.

Inflorescence size:

*Height.*—Approximately 14 cm.

*Diameter.*—Approximately 18 cm.

Inflorescence sheath:

*Length.*—Approximately 8.1 cm.

*Diameter.*—Approximately 3.6 cm, unrolled, normally very tightly held to stem.

*Texture.*—Inner Surface: Glabrous. Outer Surface: Glabrous.

*Color.*—Near RHS Greyed-Purple 183C.

Peduncle:

*Length.*—Approximately 8.5 cm.

*Width.*—Approximately 1.0 cm.

*Color.*—Near RHS Yellow-Green 146A with mottling near Greyed-Purple 187A.

*Texture.*—Glabrous.

*Strength.*—Very strong.

Flowers:

*Flower form.*—Salverform.

*Flower diameter* (*at widest point*).—Approximately 12.0 cm.

*Flower length* (*height from the base of the pedicel*).—Approximately 10.0 cm.

Flower bud: (just before showing color).

*Length.*—Approximately 4.0 cm.

*Diameter.*—Approximately 2.9 cm.

*Shape.*—Ovoid.

*Color.*—Near RHS Red-Purple 59B.

Bracts:

*Quantity.*—Average 3.

*Arrangement.*—Whorled.

*Length.*—Approximately 4.0 cm.

*Width.*—Approximately 1.5 cm.

*Shape.*—Elliptic.

*Apex.*—Acute.

*Margin.*—Entire.

*Texture.*—Glabrous.

*Appearance.*—Shiny.

*Color.*—Inner Surface: Near RHS Yellow-Orange 16B with stripes near Red 53B. Outer surface: Near RHS Orange 28B with stripes near Red 53B.

Pedicels:

*General description.*—Flattened.
*Length.*—Approximately 0.5 cm.
*Diameter.*—Approximately 0.7 cm.
*Angle.*—About 45 degrees from Peduncle.
*Strength.*—Very strong.
*Texture.*—Succulent, glabrous.
*Color.*—Near RHS Yellow-Green 144C.

Pedicel sheath:

*Texture.*—Glabrous.
*Length.*—Approximately 1.0 cm.
*Width.*—Approximately 1.1 cm.
*Color.*—Near RHS Greyed-Purple 187A.

Sepals:

*Quantity.*—Average 3.
*Appearance.*—Slightly shiny.
*Length.*—Approximately 1.1 cm.
*Width.*—Approximately 0.9 cm.
*Shape.*—Ovate.
*Apex.*—Acute.
*Base.*—Obtuse.
*Margin.*—Entire.
*Texture.*—Glabrous.
*Color.*—Inner Surface: Near RHS Yellow-Green 146A with stripes and margin near Red-Purple 59A. Outer Surface: Near RHS Red-Purple 59A with stripes near Yellow-Green 146C.

Petals:

*Quantity.*—4 actual petals; 2 petaloid staminoides described in separate section.
*Arrangement.*—Whorled.
*Length.*—Approximately 8.4 cm.
*Width.*—Approximately 5.0 cm.
*Shape* (*all petals*).—Spatulate.
*Apex* (*all petals*).—Obtuse, with 2 obtuse shallowlobes. Depth of lobe: approximately 0.3 cm.
*Base.*—Cuneate.
*Margin.*—Entire.
*Texture.*—Inner surface: Glabrous.
*Texture.*—Outer surface: Glabrous. Color: When opening, inner and outer surfaces: Near RHS Red 45D. Fully opened, inner surface: Near RHS Orange-Red 35A, base flushed Red 47C. Fully opened, outer surface: Near RHS Orange-Red 35A, base flushed Red 47C. Fading inner surface: Near RHS Red 48B. Fading outer surface: Near RHS Red 51A.

Primary/largest petaloid staminodia:

*Quantity.*—1.
*Length.*—Approximately 6.3 cm.
*Width.*—Approximately 1.0 cm.
*Shape.*—Narrow oblanceolate, asymmetrical.
*Apex.*—Acute, curling.
*Base.*—Obtuse.
*Margin.*—Entire.
*Texture.*—All surfaces glabrous.
*Appearance.*—Shiny.
*Color.*—Upper (inner) surface: Near RHS Red 45D with stripes near Orange-Red 35A.
*Color.*—Lower (outer) surface: Near RHS Red 47A with stripes near Orange-Red 35A. Stamen Present on Primary Petaloid staminoidia.

Stamens:

*Number.*—1.
*Filament length.*—No filament.
*Anther length.*—Approximately 1.1 cm.
*Anther color.*—Near RHS Orange 26B.
*Anther shape.*—Linear, undulating.
*Pollen.*—Moderate.
*Pollen color.*—Near RHS Orange 26D.

Secondary petaloid staminode:

*Quantity.*—1.
*Length.*—Approximately 4.1 cm.
*Width.*—Approximately 0.5 cm.
*Shape.*—Linear.
*Apex.*—Acute.
*Base.*—Obtuse.
*Margin.*—Entire.
*Texture.*—Upper (inner) and lower (outer) surfaces: Glabrous.
*Appearance.*—Shiny.
*Color.*—Upper (inner) surface: Near RHS Red 47 B with stripes near Yellow 13C.
*Color.*—Lower (outer) surface: Near RHS Red 47 B with stripes near Yellow 13C.

Fragrance: Very faint.

REPRODUCTIVE ORGANS

Stamens: See Primary petaloid staminode.

Gynoecium:

*Pistil.*—Ovary present, no visible stigma or style. Ovary color: Near RHS Yellow-Green 144B. Ovary diameter: 0.3 cm. Ovary height: 0.5 cm.

OTHER CHARACTERISTICS

Seeds: Infrequent, low production of round, approximately 0.6 cm diameter seeds near RHS Brown 200B.

Disease/pest resistance: Neither resistance nor susceptibility to common diseases and pets of *Canna* have been observed in the new variety.

Temperature tolerance: Tolerates temperatures from approximately 4° C. to 38° C.

What is claimed is:

1. A new and distinct cultivar of *Canna generalis* plant named 'Can Do Apricot Dark Leaf' as herein illustrated and described.

* * * * *